United States Patent [19]

Zhan et al.

[11] Patent Number: 5,626,564
[45] Date of Patent: May 6, 1997

[54] ADJUSTABLE SIDEHOLES CATHETER

[75] Inventors: Xiao X. Zhan; Patricia E. Thorpe, both of Omaha, Nebr.

[73] Assignee: Creighton University, Omaha, Nebr.

[21] Appl. No.: 414,298

[22] Filed: Mar. 31, 1995

[51] Int. Cl.⁶ .................................................. A61M 5/178
[52] U.S. Cl. .......................... 604/164; 604/246; 604/280; 604/283; 604/170
[58] Field of Search ...................... 604/158, 164, 604/96–103, 246–249, 280–284, 264, 170

[56] References Cited

U.S. PATENT DOCUMENTS

| | | |
|---|---|---|
| 4,468,224 | 8/1984 | Enzmann et al. . |
| 4,772,266 | 9/1988 | Groshong . |
| 5,024,655 | 6/1991 | Freeman et al. . |
| 5,215,527 | 6/1993 | Beck et al. . |
| 5,346,467 | 9/1994 | Coll . |
| 5,478,329 | 12/1995 | Ternamian . |

*Primary Examiner*—Vincent Millin
*Assistant Examiner*—Perry E. Van Over
*Attorney, Agent, or Firm*—Benjamin Aaron Adler

[57] ABSTRACT

The present invention provides an adjustable sideholes catheter, comprising an inlying catheter having multiple sideholes on its distal side; and an outlying catheter having an irrigation port on its proximal side. Further described are uses for an adjustable sideholes catheter.

18 Claims, 3 Drawing Sheets

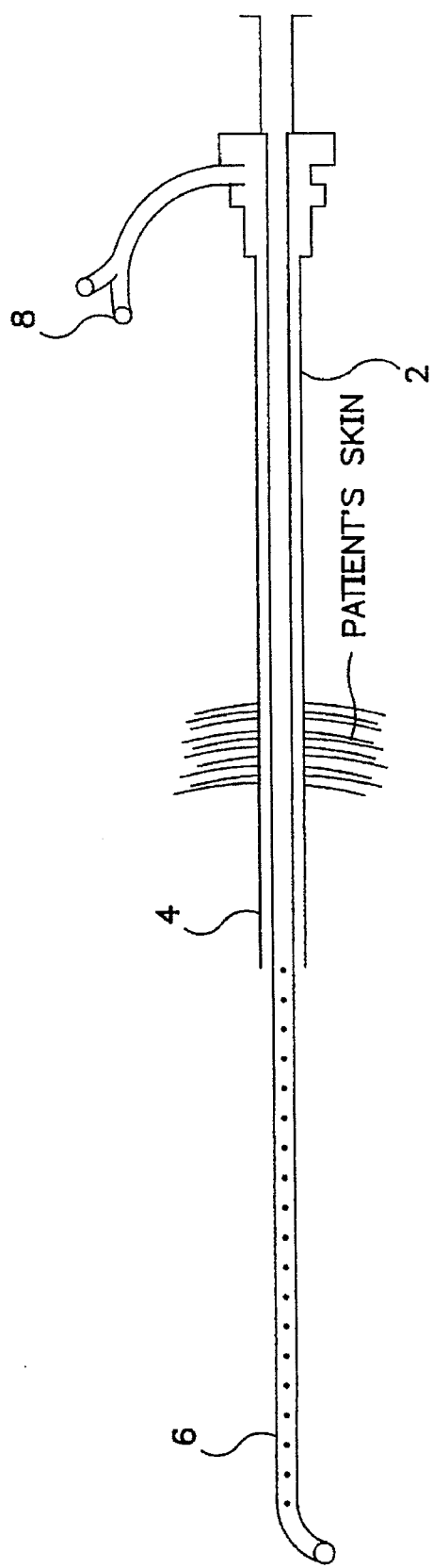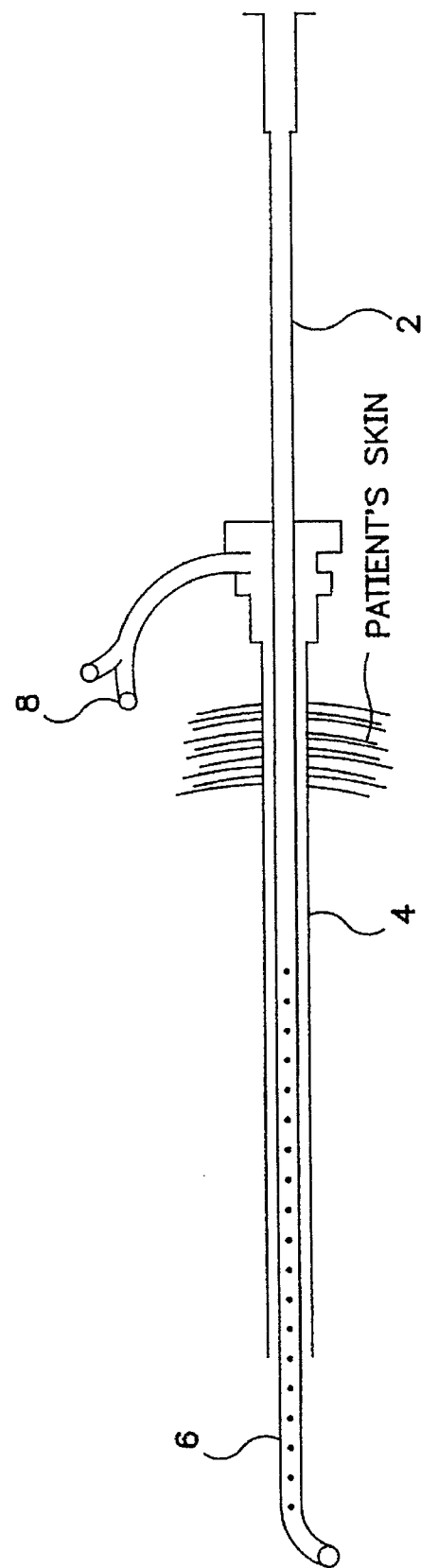

ADJUSTABLE SIDEHOLES CATHETER

BACKGROUND OF THE INVENTION

1. Field of the Invention

The present invention relates generally to the fields of interventional radiology and medical devices. More specifically, the present invention relates to a novel adjustable sideholes catheter for use in treating, inter alia, venous or arterial thrombus by regulating both the injection site and volume of drug injected.

2. Description of the Related Art

Catheters are being used increasingly as a means for delivering diagnostic or therapeutic agents to internal target sites that can be accessed through the circulatory system. For example, in angiography, catheters are designed to deliver a radio-opaque agent to a target site within a blood vessel, to allow radiographic viewing of the vessel and of the blood flow characteristics near the release site. For the treatment of localized disease, such as solid tumors, catheters allow a therapeutic agent to be delivered to the target site at a relatively high concentration with minimal side effects.

U.S. Pat. No. 4,739,768 describes a catheter having a guide wire. The catheter may be guided from an external body access site such as through the femoral artery, to an internal tissue site. The catheter progresses through a tortuous path of at least about 5 cm through vessels of less than about 3 mm inner diameter.

Catheters with multiple tiny sideholes over a length of 5 to 15 cm on the distal end of catheter have been used in thrombolytic therapy for many years. The lower rate of infusion (1–2 ml/minute) of thrombolytic drugs was widely employed in routing procedures. However, thrombolytic drugs only pass through a few proximal sideholes when this lower rate of infusion (1–2 ml/minute) was used. Consequently, most drugs are diverted into the blood circulation and never reach the target thrombus. This effect found with prior art catheters has resulted in a devaluation of local thrombolytic therapy, especially when such a technique is indicated for venous thrombolytic therapy. Thus, high doses of drugs become diluted entering the blood flow and pass through systemic circulation. This is, therefore, one of factors that make venous catheter-directed thrombolytic therapy longer than local arterial thrombolytic therapy. No prior art methods or catheters to avoid this phenomenon have been reported.

The prior art is deficient in the lack of effective means of treating, inter alia, venous or arterial thrombus with a controllable injection site and volume. The present invention fulfills this longstanding need and desire in the art.

SUMMARY OF THE INVENTION

In one embodiment of the present invention, there is provided an adjustable sideholes catheter, comprising an inlying catheter having multiple sideholes on its distal side; and an outlying catheter having an irrigation port on its proximal side.

Other and further aspects, features, and advantages of the present invention will be, apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A and 1B are a prototype of the present invention illustrating the primary components of a preferred embodiment. FIG. 1A shows the set of the catheter. FIG. 1B shows the outlying catheter moving forward to close the proximal sideholes.

DETAILED DESCRIPTION OF THE INVENTION

Figure 2A:
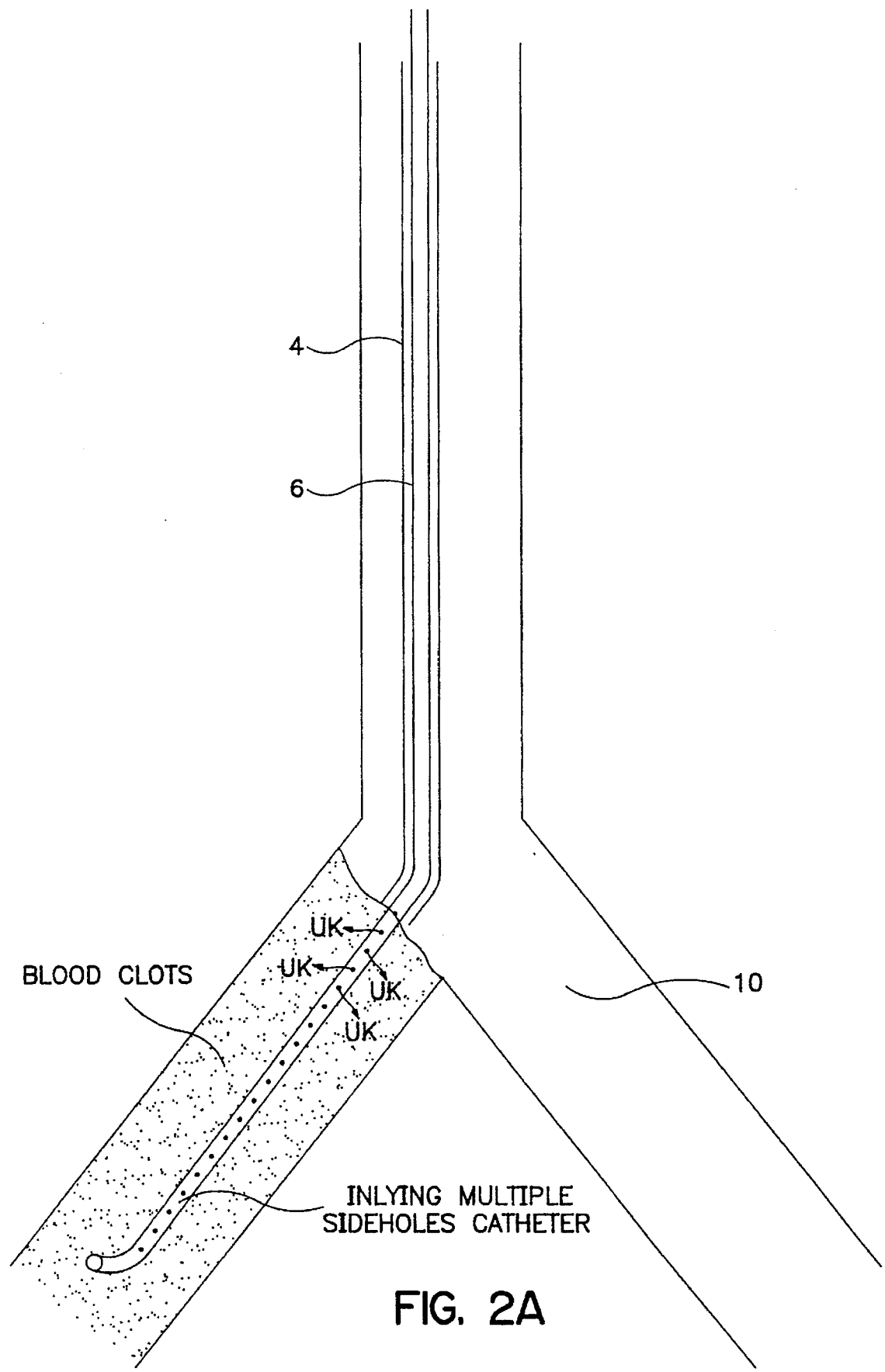
FIGS. 2A and 2B are drawings that show how the catheter is used in venous thrombolytic therapy in vivo.

The present invention is directed to a novel catheter. In one particular embodiment, the adjustable sideholes catheter of the present invention may be used to adjust the injection site and flow rate in thrombolytic therapy for venous thrombus. In one embodiment, the adjustable sideholes catheter consists of a set of coaxial catheters. The inlying catheter has multiple sideholes on its distal part between two radiopaque markers and the outlying catheter or sheath has an irrigation port (side-arm) on its proximal part. Both catheters are made of, in one embodiment, lower frictional polyethylene materials. The size of outlying catheter is preferably just a little larger than the inlying catheter. Both parts of the catheter of the present invention can be moved back-and-forth smoothly. The outlying catheter should be long enough to reach the nearest sidehole of the inlying catheter when the proximal parts of the two catheters are attached. Clear marks should be given on the proximal part of inlying catheter to assist evaluating the location of distal end of outlying catheter. The length, size and shape of both catheters are variable. A standard set of catheters can be made for general application. A method of dissolving venous thrombosis is also described.

The adjustable sideholes catheter of the present invention is of great value in the following situations: (1) to simplify catheterization of angiography by adjusting the outlying catheter to control the number of functional sideholes on the inlying catheter. This will reduce the change of the end hole catheter to multiple sideholes catheter in certain situations; (2) to facilitate the selection of a vessel orifice by moving a straight outlying catheter back and forth on a curved inlying catheter; (3) to allow removal of blood clots through outlying catheter; (4) for introduction of non-tapered catheters to remote targets; (5) for introduction of closed-tapped catheters; (6) for introduction of interventional devices such as atherectomy devices; and (7) to permit measurement of blood pressures.

The following examples are given for the purpose of illustrating various embodiments of the invention and are not meant to limit the present invention in any fashion.

A catheter for adjusting the injection site and flow rate in thrombolytic therapy on venous thrombus was designed. It consists of a set of coaxial catheters. The inlying catheter has multiple sideholes on its distal part between two radiopaque markers and the outlying catheter or sheath has an irrigation port (side-arm) on its proximal part. Both catheters are made of lower frictional polyethylene materials.

The size of the outlying catheter should be barely larger than the inlying catheter. Both catheters should be able to be moved back-and-forth smoothly. The outlying catheter should be long enough to reach the nearest sidehole of the inlying catheter when the proximal parts of the two catheters are attached. Clear marks should be given on the proximal part of inlying catheter to assist evaluating the location of distal end of outlying catheter. The inlying catheter has 5 to 20 sideholes (approximately 0.009 inch diameter) spirally arranged between two distal radiopaque markers. The interval of each sidehole is approximately 0.5 cm. A 0.032-inch or 0.035-inch guide wire can be freely advanced beyond the inlying catheter tip. A catheter introduction sheath can be used in the introduction of the adjustable sideholes catheter into the blood vessels. The size of sheath can be 6 F–9 F depend on the size of inlying catheter. The length, size and shape of both catheters are variable based on customer's requirement. A standard set of catheters can be made for general application.

The specification of a set of standard catheters, in one embodiment, is as follows;

1. Inlying catheter internal diameter: 3 F, 4 F, 5 F.
2. Inlying catheter length: 65 cm, 85 cm, 105 cm, 125 cm.
3. Length of inlying catheter with sideholes: 10 cm, 15 cm, 20 cm with two radiopaque markers on each end.
4. Intervals of each sidehole: 0.5 cm, spirally arranged.
5. Size of sideholes: approximately 0.009 inch diameter
6. Outlying catheter internal diameter: 5 F, 6 F, 7 F.
7. Outlying catheter length: 10 cm or 15 cm or 20 cm shorter than corresponding inlying catheter.
8. Outlying catheter irrigation port: 15 cm with a three way stopcock.

Modes for Using the Invention

The present invention's adjustable sideholes catheter introduces a novel procedure to dissolve clots in blood vessels. In one embodiment of a method of the present invention, when the inlying catheter is completely inserted into the blood clots, the thrombolytic drugs dissolve the proximal clots first because there is a higher concentration of drugs around the proximal sideholes. The thrombolytic drugs pass through the proximal sideholes and get into the blood flow following the continuous infusion. As the direction of venous flow is opposite to the clots, the drugs are diluted after the circulation. In order to force penetration of the drugs into the distal clots, two techniques can be used. One technique is to push the inlying catheter distally, but this requires the guidance of an X-ray machine and sometimes it is impossible to move forward due to the resistance from clots and veinal valves.

Another method is to move the outlying catheter forward to close the proximal sideholes and drive the drugs into the distal thrombus. The outlying catheter is moved in small increments periodically until the outlying catheter reaches the end of the inlying catheter. Repeating the procedure dissolves more clots distally. If it is impossible to insert all of the sideholes part of the inlying catheter into the clots, the outlying catheter can be moved forward to close the proximal sideholes without changing another less sideholes catheter. This same techniques can be used in arterial thrombosis. The above techniques taught by the instant application using the adjustable sideholes catheter of the present invention can not be replaced by using a few sideholes catheter known in the prior art. For example, the Patent Pressure Response Outlets, also known as a slits infusion catheter as described in Pat. No. 1,688,929, can not adjust the number of slits. Thus, the thrombolytic drugs may go through the slits and not into the clots resulting in a diminished local thrombolytic effect. In such a situation, the adjustable sideholes catheter of the present invention would be highly advantageous.

If the inlying catheter was made with different shape of curves on the distal part, a back and forth movement of a straight outlying catheter can adjust the curve of the inlying catheter. This technique simplifies the catheterization of angiography by adjusting the outlying catheter to control the number of functional sideholes on the inlying catheter and therefore reduce the changing of the end hole catheter to the multiple sideholes catheter in certain situations. If the inlying catheter is pulled out, the outlying catheter will allow removal of blood and introduction of nontapered catheters or closed-tapped catheter or interventional devices to remote targets or clots through the outlying catheter. A measurement of blood pressures can also be done through the outlying catheter.

A catheter introduction sheath can be used in the introduction of the adjustable sideholes catheter into the blood vessels. The size of sheath can be 6 F–9 F depending on the size of inlying catheter and outlying catheter. A continued infusion of saline with a lower rate can be given through the irrigation ports of the outlying catheter and introduction sheath.

With reference to the appended drawings, FIG. 1 illustrates one embodiment of the adjustable sideholes catheter of the present invention. The adjustable sideholes catheter 2 comprises an outlying catheter 4 and an inlying multiple sideholes catheter 6. The outlying catheter 4 has an irrigation port 8. FIG. 1A shows the adjustable sideholes catheter of the present invention with the inlying multiple sideholes catheter 6 in an extended position. FIG. 1B shows the adjustable sideholes catheter of the present invention with the inlying multiple sideholes catheter 6 in a retracted position.

Figure 2B:
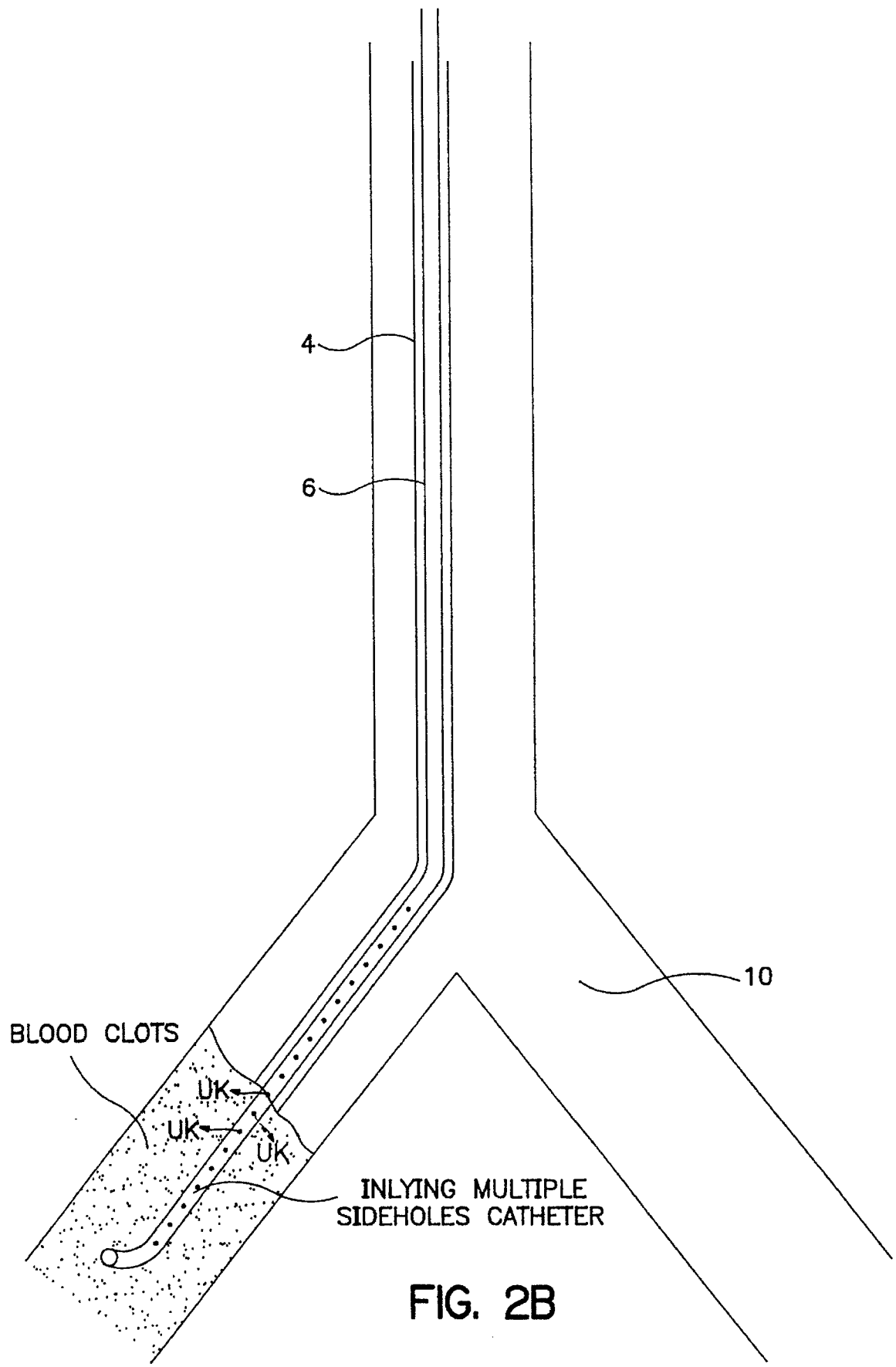

FIG. 2 illustrates the adjustable sideholes catheter of the present invention before thrombolytic therapy with the outlying catheter in a non-moving position. FIG. 2A shows both the inlying catheter 6 and the outlying catheter 4 inside a vein 10. FIG. 2B shows the outlying catheter 4 is moved forward to close the proximal sideholes of the inlying catheter 6. In this embodiment of the present invention, the outlying catheter is moved forward a few hours after post-thrombolytic therapy.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An adjustable sideholes catheter, comprising
   an inlying catheter having a distal end and a proximal end wherein said distal end has multiple sideholes and wherein said distal end has at least two discrete radiopaque marks;

an outlying catheter having a distal end and a proximal end wherein said proximal end has an irrigation port;

wherein said outlying catheter has a slightly greater diameter than said inlying catheter, enabling said outlying and inlying catheters to be moved slidably back and forth.

2. The adjustable sideholes catheter of claim 1, wherein said catheter is made of lower frictional polyethylene.

3. The adjustable sideholes catheter of claim 1, wherein said inlying catheter has multiple sideholes on its distal part between two radiopaque markers.

4. The adjustable sideholes catheter of claim 1, wherein said outlying catheter is long enough to reach the nearest sidehole of the inlying catheter when the proximal parts of the inlying and outlying catheters are attached.

5. The adjustable sideholes catheter of claim 1, wherein said inlying catheter has an internal diameter selected from the group consisting of 3 F, 4 F and 5 F.

6. The adjustable sideholes catheter of claim 1, wherein said inlying catheter has a length of from about 65 cm to about 125 cm.

7. The adjustable sideholes catheter of claim 1, wherein said inlying catheter with sideholes has a length of from about 10 cm to about 20 cm.

8. The adjustable sideholes catheter of claim 1, wherein said sideholes are spaced approximately 0.5 cm apart.

9. The adjustable sideholes catheter of claim 1, wherein said intervals of each sidehole are spirally arranged.

10. The adjustable sideholes catheter of claim 1, wherein said sideholes are approximately 0.009 inches in diameter.

11. The adjustable sideholes catheter of claim 1, wherein said outlying catheter has an internal diameter selected from the group consisting of 5 F, 6 F and 7 F.

12. The adjustable sideholes catheter of claim 1, wherein said outlying catheter has a length approximately 10 cm to about 20 cm shorter than corresponding inlying catheter.

13. The adjustable sideholes catheter of claim 1, wherein said irrigation port of said outlying catheter is a three way stopcock.

14. The adjustable sideholes catheter of claim 1, wherein a 0.032-inch to 0.035-inch guide wire is freely advanceable beyond the inlying catheter tip.

15. The adjustable sideholes catheter of claim 1, wherein a catheter introduction sheath introduces the adjustable sideholes catheter into a blood vessel.

16. The adjustable sideholes catheter of claim 1, wherein said catheter is used to simplify catheterization of angiography by adjusting the outlying catheter to control the number of functional sideholes on the inlying catheter.

17. The adjustable sideholes catheter of claim 1, wherein said catheter is used to remove blood clots through said outlying catheter.

18. The adjustable sideholes catheter of claim 1, wherein said catheter is used to measure blood pressures.

* * * * *